United States Patent [19]

Deruysscher

[11] Patent Number: 4,974,730

[45] Date of Patent: Dec. 4, 1990

[54] CLEAN UP KIT

[76] Inventor: Betty K. Deruysscher, 1257 Lindell Dr., Walnut Creek, Calif. 94598

[21] Appl. No.: 53,728

[22] Filed: May 26, 1987

[51] Int. Cl.$^5$ .............................................. B65D 69/00
[52] U.S. Cl. ................................... 206/581; 206/223; 206/812; 15/227; 15/104.93; 604/289
[58] Field of Search ................. 604/289, 290; 15/227, 15/104.93, 104.94; 206/38, 223, 225, 233, 570, 812, 581

[56] References Cited

U.S. PATENT DOCUMENTS

| | | | |
|---|---|---|---|
| 1,551,416 | 8/1925 | Marshall | 15/227 |
| 1,731,340 | 10/1929 | Lambert | 15/227 X |
| 1,782,502 | 11/1930 | Crane | 15/227 |
| 2,621,784 | 12/1952 | Boytham | 15/227 X |
| 2,790,982 | 5/1957 | Schneider | 15/227 X |
| 2,840,080 | 6/1958 | Clark | 128/296 |
| 2,999,265 | 9/1961 | Duane et al. | 604/289 X |
| 3,240,326 | 3/1966 | Miller | 206/46 |
| 3,264,188 | 8/1966 | Grersham | 167/84 |
| 3,363,625 | 1/1968 | Jovis | 604/289 |
| 3,414,927 | 12/1968 | Worcester | 15/104.93 |
| 3,561,456 | 2/1971 | Stuart, Jr. | 132/79 |
| 4,427,111 | 1/1984 | Laipply | 206/210 |
| 4,498,590 | 2/1985 | Burdick | 206/581 |
| 4,553,665 | 11/1985 | Weick et al. | 206/37 |

FOREIGN PATENT DOCUMENTS 086355  8/1983  European Pat. Off. ............ 604/289

Primary Examiner—William I. Price

[57] ABSTRACT

A kit for cleaning up male and female bodies after intercourse having a male clean up device in the form of a rectangular flat pouch and a generally flat female clean up member positionable in such pouch both before and after use, the pouch and female clean up member being formed of a flexible material having a liquid absorbent layer and a layer impermeable to liquid. In one form of the invention the impermeable layer is on the outside of the pouch, the pouch is turned inside out for use, and is then turned back to its original condition. In another form of the invention, the liquid absorptive layer is on the outside of the pouch for easy use and the pouch is then turned inside out to present the water impermeable layer on the outside.

8 Claims, 1 Drawing Sheet

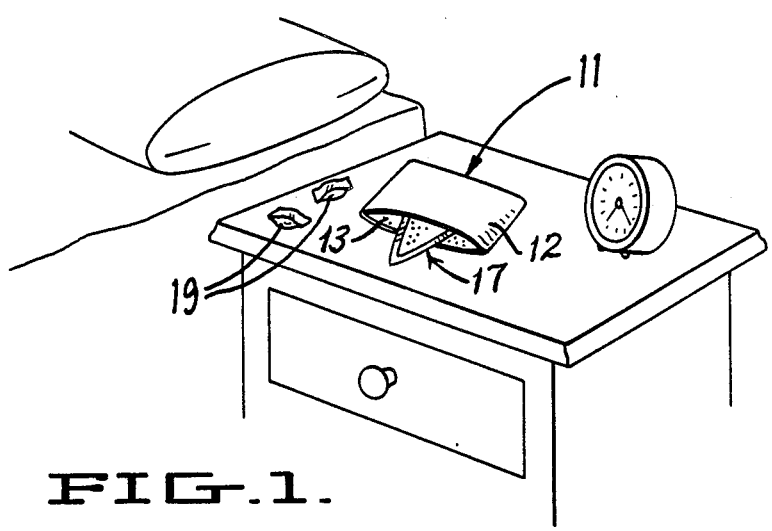
FIG. 1.
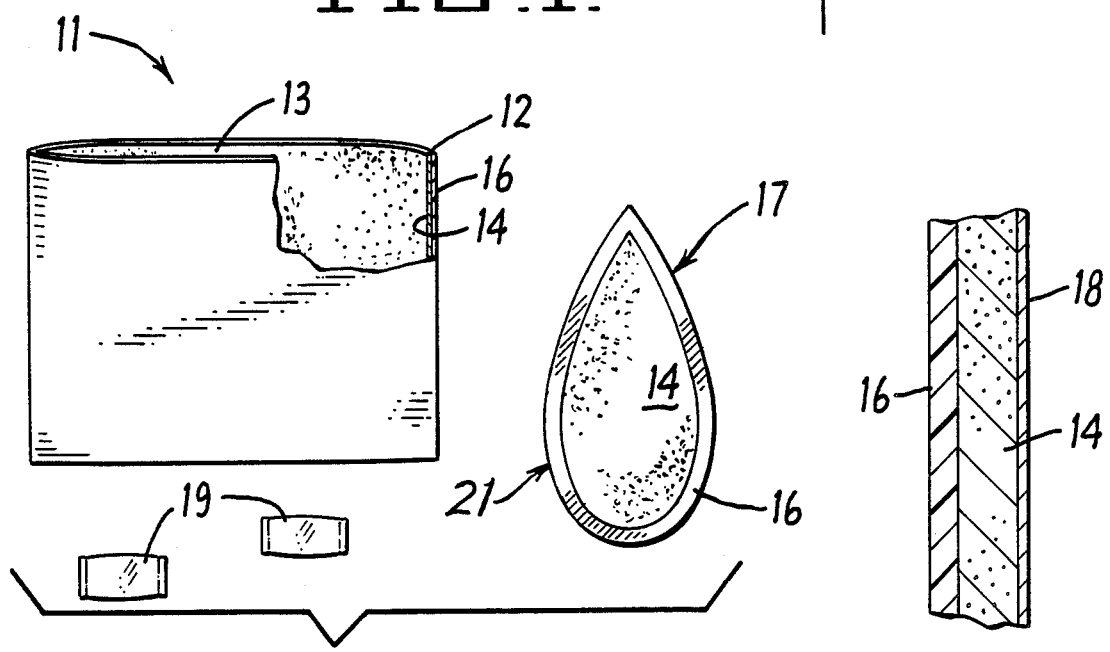
FIG. 2.
FIG. 3.
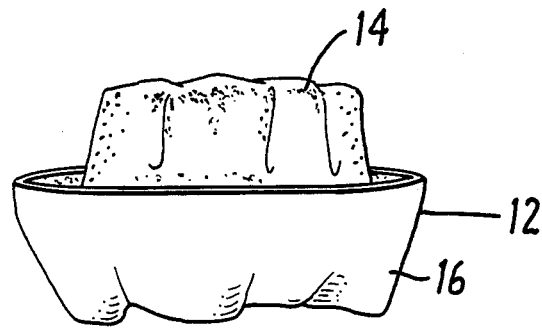
FIG. 4.
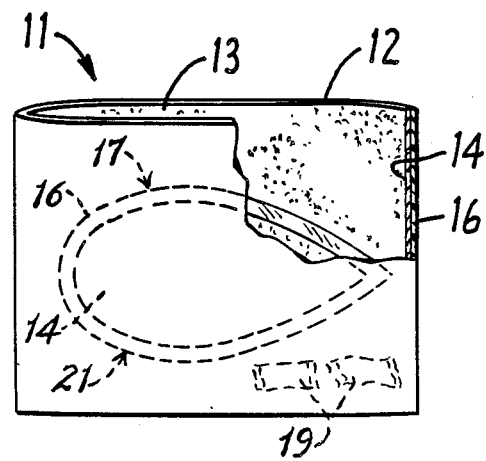
FIG. 5.

CLEAN UP KIT

BACKGROUND OF THE INVENTION

1. Field of the Invention

This invention relates to cleansing devices, and more particularly to devices having a plurality of parts and sold together as a kit.

2. Description of the Prior Art

Many devices have been proposed for cleaning unwanted materials from the skin. Perhaps the best known of these are moistened towlettes made of moisture proof paper and folded up to fit within a waterproof envelope. These towlettes are widely sold for use in cleaning food and grease from the fingers of the user after partaking of fried chicken and other fast foods. Such a cleaning device may be found in U.S. Pat. No. 3,414,927 issued Dec. 10, 1968 to G. S. Worcester.

Variations of the towlettes are proposed for more specialized use, such as proctological use or for use by persons suffering from anorectal disorders. These are used for cleaning the anus and surrounding areas of the human body. Typically, surfactants and emollients may be added to the liquid used to premoisten the towlettes. Examples of these devices are found in U.S. Pat. Nos. 2,840,080 issued Dec. 18, 1956 to M. Clark and 3,264,188 issued Aug. 2, 1966 to J. Gresham.

The only prior art devices known to applicant which are capable of cleaning liquid or moist material from the skin of the user are pads of gauze and the like. Such pads are not self-protecting against dirt and contamination and therefore must be placed in separate containers for transportation or storage.

Other patents showing various approaches to skin cleansing devices are listed as follows:

| Patent No. | Inventor |
|---|---|
| 3,240,326 | W. S. Miller |
| 3,561,456 | C. W. Stuart, Jr. |
| 4,427,111 | T. C. Laipply |
| 4,498,590 | L. M. Burdick |
| 4,553,665 | H. H. Weick, et al. |

The above-listed patents are believed to be relevant to the present invention because they were adduced by a prior art search made by an independent searcher, and a copy of each of the above-listed patents is supplied to the Patent and Trademark Office herewith.

The term "prior art" as used herein or in any statement made by or on behalf of applicant means only that any document or thing referred to as prior art bears, directly or inferentially, a date which is earlier than the effective date of this application.

No representation nor admission is made that any of the above-listed documents is part of the prior art in any acceptation of that term, or that no more pertinent information exists.

SUMMARY OF THE INVENTION

The present invention is particularly designed for use by men and women after sexual intercourse to clean liquid and wet materials from their skin. Often, facial tissues or wash cloths are used for such purposes, but tissues are prone to become sodden and tear apart and cloths have to be washed. The used tissues are difficult to dispose of, and washing cloths can be distasteful.

The male and female clean up kit of the present invention includes a flat, rectangular pouch formed for opening along one of its longer sides for removably containing a generally flat member. The pouch and removable flat member are formed of a flexible material having a dry, liquid absorbent layer and a second layer impermeable to liquid.

Normally, the pouch is used to clean up the male, and the generally flat member is removed from the pouch and used to clean up the female. Because of the extremely sensitive nature of the areas of skin which are to be cleaned, the surface which contacts the skin must be extremely soft and non-abrasive. The skin contacting surface of the celluosic absorbent material can be made to provide the desired softness and non-abrasiveness or, in the alternative, a third layer of water permeable material may be used, and this third layer can be made to possess the desired softness and non-abrasiveness.

In one form of the invention, the plastic, water impervious layer is on the outer side of the pouch so as to keep the contents clean until use. At the time clean up is desired, the female clean up unit and any other enclosed materials are removed from the pouch and it is turned inside out to expose the water absorptive surface. When clean up has been accomplished, the pouch is again turned right side out and the female clean up device and other materials are enclosed within the pouch.

In another form of the invention, the water absorptive surface is on the outer side of the pouch and the entire unit is encased in a removable protective covering. For use, the protective covering is removed from the pouch, the female unit is removed from the pouch, and clean up is accomplished. As soon as clean up is finished, the pouch is turned inside out so that the water impermeable plastic layer is on the outside. The female unit and any other materials such as the original protective covering, are placed within the pouch.

In accordance with the invention, lubricants and emollients suitable for use before intercourse are packed in tearable flat capsules positioned within the pouch. The female clean up sheet is of elongated tear shape sized and proportioned to fit in the crotch of the female in overlying relation to the sexual organs. The female clean up sheet is capable of being retained for some period of time in this position to absorb any dribbles, especially by coating the edge of the female clean up sheet with a lubricant such as petroleum jelly.

It is therefore a principal object of the present invention to provide a male and female clean up kit having separate units for cleaning the genital areas of the male and the female.

Another object of the present invention is to provide a male and female clean up kit of the character described in which the surfaces contacting the skin of the user during clean up are dry and highly water absorbent.

A further object of the present invention is to provide a male and female clean up kit of the character described in which the female clean up unit is positioned within a pouchshaped male clean up unit, along with capsules of lubricants and emollients for use prior to and during the cleaning process.

A further object of the present invention is to provide a male and female clean up kit in which the male and female units are both formed of biodegradable sheet material having a layer of dry, liquid absorbent material and a layer of thin, flexible water impervious plastic material.

3

Other objects and features of advantage will become apparent as the specification progresses and from the claims.

BRIEF DESCRIPTION OF THE DRAWINGS

FIG. 1 is a perspective view of a male and female clean up kit constructed in accordance with the present invention and having its contents partially removed.

FIG. 2 is a plan view on an enlarged scale of a pouch forming part of the kit of FIG. 1 and a female clean up unit removed from the pouch, together with capsules of lubricants, emollients and the like.

FIG. 3 is a fragmentary cross-sectional view on a greatly enlarged scale of the material from which the male and female clean up units of FIG. 2 are made.

FIG. 4 is a perspective view of the pouch of FIG. 2 being turned inside out.

FIG. 5 is a perspective view similar to that of FIG. 2, but showing the female clean up unit and the expended capsules placed within the pouch for disposal after use.

While only the preferred forms of the invention are illustrated in the drawings, it will be apparent that various modifications could be made without parting from the ambit of the claims.

DESCRIPTION OF THE PREFERRED EMBODIMENTS

As may be seen in the accompanying drawings, the male and female kit 11 of the present invention provides a rectangular flat pouch 12 formed for opening along one of its longer sides 13, the pouch 12 being formed of a flexible material having a liquid absorbent layer 14 and a layer 16 impermeable to liquid whereby the pouch is adapted for cleaning away liquid and moist material from the male after intercourse, and a generally flat female clean up unit 17 formed of a sheet of material similar to that of the pouch 12, with the female unit 17 being removably contained within the pouch 12 and adapted for cleaning away and confining liquid and moist material on the female.

In the form of the invention illustrated in FIG. 3 of the drawings, the flexible material from which pouch 12 and unit 17 are formed also has a liquid permeable layer 18 on the side of the liquid absorbent layer 14 remote from the liquid impermeable layer 16. The layer 14 may be of any suitable dry and highly absorbent flexible material such as felted cellulosic material, and the water impermeable layer 16 is preferably of a thin layer of flexible plastic such as polyethylene. The water permeable layer 18 may be of any suitable form such as an open mesh cotten cloth having the softness and smoothness requisite for cleaning very sensitive skin areas without undue discomfort.

In the form of the invention illustrated in FIG. 2 of the drawings, the liquid impermeable layer 16 is on the outer side of the pouch for protecting the pouch and its contents prior to use. The pouch 12 is capable of being turned inside out, as illustrated in FIG. 4 of the drawings so as to expose the liquid absorbent layer 14 for removing liquid and moist material from the male. The pouch is further capable of being turned back to its original condition with the liquid impermeable layer 16 on the outside of the pouch for protecting against of liquid and moist material from therein.

In the form of the invention illustrated in FIG. 5 of the drawings, the pouch is constructed with the water absorptive layer 14 on the outside and the plastic layer 16 on the inside. In both forms of the invention, the female clean up unit 17 and any capsules 19 are packed within the pouch 12. When it is desired to use the clean up kit, the unit 17 and capsules 19 are removed therefrom. The units 12 and 17 are then used to clean up moisture and moist materials separately from the male and the female users. The used unit 17 is then returned to the interior of the pouch 12 where the liquid impervious coating on the outside of the pouch protects the interior and contents against leaking.

As may best be seen in FIG. 2 of the drawings, the generally flat female clean up unit 17 is of elongated teardrop outline proportioned to fit within the female crotch in overlying relation to the sexual organs and with the liquid impermeable layer 16 on the side opposite to the user's body whereby the layer 14 absorbs liquid and moist material emanating from the user's body thereat.

Unit 17 will normally stay in place in the crotch while absorbing liquid, and this propensity is enhanced by applying a coating of petroleum jelly to the peripheral edge 21 of the unit 17, as illustrated in FIG. 2 of the drawings.

Preferably, to facilitate disposal of the used kit, the components are made of biodegradable material. The water impermeable layer 16 can be made extremely thin and of a plastic material which, when exposed to oxygen or ultraviolet soon decomposes. The kit is compact, flexible, light in weight, and is suitable for flushing down toilets.

From the foregoing it will be seen that the male and female clean up kit of the present invention provides a novel and meritorious sanitary device for effectively removing liquid and moist materials from the users' bodies and confining such materials for disposal.

What is claimed is:

1. A male and female clean up kit, comprising
a rectangular flat pouch having an opening along one of its longer sides,
said pouch being formed of a flexible material having a liquid absorbent layer and a layer impermeable to liquid whereby said pouch is adapted for cleaning away liquid and moist material from the male after intercourse,
and a generally flat member of similar material removably contained within said pouch and adapted for cleaning away and confining liquid and moist material on the female.

2. A male and female clean up kit as described in claim 1, and wherein said flexible material also has a liquid permeable layer on the side of said liquid absorbent layer remote from said liquid impermeable layer.

3. A male and female clean up kit as described in claim 1, and wherein said liquid impermeable layer is formed from flexible sheet plastic and is on the normal outside of said pouch for protecting said pouch and its contents, said pouch being capable of being turned inside out so as to expose said liquid absorbent layer for removing said liquid and moist material, said pouch further being capable of being turned back to its original condition with said liquid impermeable layer on the outside of said pouch for protecting against loss of said liquid and moist material from therein.

4. A male and female clean up kit as described in claim 1, and wherein said generally flat member is of elongated teardrop outline proportioned to fit within the female crotch in overlying relation to the sexual organs and with said liquid impermeable layer on the side opposite to the user's body whereby said liquid absorbent layer absorbs liquid and moist material on the user's body thereat.

5. A male and female clean up kit as described in claim 4, and wherein said generally flat member is formed for replacement in said pouch after use for disposal.

6. A male and female clean up kit as described in claim 1, and wherein said liquid impermeable layer is formed from flexible sheet plastic, and is on the normal inside of said pouch whereby turning of said pouch inside out after use confines said liquid absorbent layer therewithin.

7. A male and female clean up kit, comprising
a rectangular flat pouch formed for opening along one of its longer sides,
said pouch being formed of a flexible material having a liquid absorbent layer and a layer impermeable to liquid whereby said pouch is adapted for cleaning away liquid and moist material from the male after intercourse,
a generally flat member of similar material removably contained within said pouch and adapted for cleaning away and confining liquid and moist material on the female,
said liquid absorbent layer being formed of dry felted cellulose having high absorptive capacity,
said layer impermeable to liquid being formed of a thin flexible polyester plastic,
and at least one flat flexible capsule removably containing a lubricant carried within said pouch.

8. A male and female clean up kit as described in claim 7, and wherein said lubricant is petroleum jelly, and said generally flat member is formed for receiving a strip of petroleum jelly around its periphery for removably adhering to the body of the user at the crotch.

* * * * *